United States Patent [19]

Pelkie

[11] Patent Number: 5,733,628
[45] Date of Patent: Mar. 31, 1998

[54] BREATHABLE ELASTIC POLYMERIC FILM LAMINATES

[75] Inventor: James E. Pelkie, Terre Haute, Ind.

[73] Assignee: Tredegar Industries, Inc., Richmond, Va.

[21] Appl. No.: 729,629

[22] Filed: Oct. 10, 1996

[51] Int. Cl.[6] .............................. D03D 17/00; B32B 3/10
[52] U.S. Cl. ........................... 428/138; 442/293; 442/399
[58] Field of Search ..................... 442/293, 399; 428/138

[56] References Cited

U.S. PATENT DOCUMENTS

| | | | |
|---|---|---|---|
| 4,211,808 | 7/1980 | Trankle | 442/293 X |
| 4,317,792 | 3/1982 | Raley et al. | 264/504 |
| 4,970,259 | 11/1990 | Mitchell et al. | 524/505 |
| 4,995,930 | 2/1991 | Merz et al. | 156/209 |
| 5,034,078 | 7/1991 | Hodgson, Jr. et al. | 156/85 |
| 5,068,138 | 11/1991 | Mitchell et al. | 428/36.8 |
| 5,171,238 | 12/1992 | Kajander . | |
| 5,176,672 | 1/1993 | Bruemmer et al. . | |
| 5,336,554 | 8/1994 | Knight | 428/230 |
| 5,376,430 | 12/1994 | Swenson et al. | 428/152 |
| 5,422,172 | 6/1995 | Wu | 428/230 |
| 5,422,178 | 6/1995 | Swenson et al. | 428/343 |
| 5,462,708 | 10/1995 | Swenson et al. | 264/174 |

FOREIGN PATENT DOCUMENTS 2267055  11/1993  United Kingdom .

OTHER PUBLICATIONS

NERAC Search, pp. 1–14, Aug. 5, 1996.

*Primary Examiner*—Daniel Zirker
*Attorney, Agent, or Firm*—Emch, Schaffer, Schaub & Porcello Co., L.P.A.

[57] ABSTRACT

An elastomeric breathable three-dimensional composite material and the process for producing the same are disclosed. A carrier material is supplied onto a top surface of continuous portions of an elastomeric film to form the composite material. A pressure differential is applied to a bottom surface of film for a period of time sufficient for three-dimensional apertured structures to be formed in the film.

11 Claims, 3 Drawing Sheets

BREATHABLE ELASTIC POLYMERIC FILM LAMINATES

TECHNICAL FIELD

The present invention relates to a highly elastic breathable film laminate made by a vacuum forming lamination process. The resulting laminate is useful in disposable products such as diapers and hygiene products.

BACKGROUND OF THE INVENTION

Various processes for bonding thermoplastic films to non-woven webs or other thermoplastic films are known. The present invention is an improvement over the current state of the art non-woven laminate films. The assignee herein, Tredegar Industries is a leader in developing both non-woven/film laminated composites and formed three-dimensional film technology. For example, the Raley U.S. Pat. No. 4,317,792 relates to a formed three-dimensional film and the method for making such a film. In addition, the Merz U.S. Pat. No. 4,995,930 relates to a method for laminating a non-woven material to a non-elastic film.

Various types of formed elastic films and processes for making these films are known. The Wu U.S. Pat. No. 5,422,172 proposed an elastic laminate formed by incremental stretching of the web. However, the resulting the film has a 10% permanent set after 50% elongation which is considered to be a low performance elastic material. Further, the vapor or air permeability of the product is achieved by providing mechanical microvoids.

The Swenson et al. U.S. Pat. Nos. 5,462,708; 5,422,178; and 5,376,430 discloses elastic film laminates having an elastic core layer and at least one polymeric skin layer. However, these films are non-breathable films. There is no suggestion of utilizing a non-woven material as a skin contact layer. Further, the processes of the Swenson et al. patents would require additional materials and processing steps in order to utilize a breathable non-woven material.

The Hodgson et al. U.S. Pat. No. 5,304,078 discloses a method for forming a heat shrinkable film that exhibits elastic properties only after being shrunk. The product produced by the '078 patent is not breathable and does not utilize a non-woven composite material.

The Knight U.S. Pat. No. 5,336,554 discloses a porous elastomeric film wherein air permeability is provided by the use of laser perforation. The '554 patent proposed a high cost manufacturing process in order to achieve breathability for elastic films and laminates.

The Mitchell et al. U.S. Pat. Nos. 5,068,138 and 4,970,259 disclose the use of blown film to produce a of non-breathable elastomeric films. The '138 and the '259 patents do not address, handle or process the inherently tacky elastomeric film. Further neither patent suggested laminating the elastomeric film to a non-woven material.

There is considerable difficulty in working with and processing elastomeric films to form useful products. The inherent tacky and stretchy characteristics of elastomeric films make the films extremely difficult to process. It is especially difficult to use any elastomeric film as a layer in a multilayer laminate.

The present invention addresses those concerns discussed above. The inherently tacky nature of elastomeric film compositions makes the films difficult to use. For example, in hygiene products, only a small piece of the stretchy material might be used. The steps of removing the film from a roll or festoon, cutting the film to size, and moving the cut film are all hindered by the films' tendency to stick to the processing equipment. The prior art required the use of non-tacky thermoplastic skin layers in order to handle the elastic film in further processing steps.

Further, as products with greater elasticity are used in medical and hygiene applications, skin care issues increase. The more stretchable elastic products conform better to the body so breathability from around any loose fitting perimeter of the product is greatly reduced. The closer fit of the elastic product decreases the air flow to the skin, thus increasing the tendency for the skin to remain undesirably moist.

There is still a continuing need for improved elastic film laminates. It is desirable to provide an elastic film laminate which can be readily incorporated into a finished product without the use of adhesive materials or other additional processing steps. It is also desirable to further improve the elastic films by making the elastomeric films breathable or vapor permeable. The elastic breathable laminate films are useful in disposable products and the like where skin irritation is a concern.

The present invention overcomes the drawbacks described above and provides a breathable and elastomeric laminate comprising an elastomeric film laminated to a non-woven material. The breathable elastomeric laminate of the present invention is formed in a single processing step without the need for additional adhesive materials.

DISCLOSURE OF THE INVENTION

The present invention relates to a highly elastic breathable film laminate comprising a three-dimensional elastomeric film layer and a carrier or support web layer. It is to be understood that the terms "elastic" and "elastomeric" can be used interchangeably, and that both terms are within the contemplated scope of the present invention. These terms, "elastic" and "elastomeric", relate to materials which are stretchable under force and are recoverable as to the material's original or essentially original form upon release of the extension force.

The carrier material provides the desired mechanical properties needed for handling of the elastic film laminate and for conversion of the laminate to a finished product. In various embodiments, the carrier web can comprise a thermoplastic film material or a fibrous material. The fibrous material can comprise a fibrous web, woven and/or non-woven materials.

The high stretch, elastomeric film laminate of the present invention combines the advantages of elasticity as well as breathability. It is contemplated that the high stretch elastic film laminate of the present invention can be incorporated as a layer in various types of end use products. The resulting elastic film laminate is useful for disposable products, such as side panels in diapers and hygiene products, and for medical applications, such as wound dressings and bandages.

According to one embodiment of the present invention, a predetermined thickness of a layer of a carrier material is introduced onto a top surface of an elastomeric film material just prior to or directly at the point of forming the three-dimensional characteristics of the film. The carrier material is supplied under an appropriate tension to the film material. In preferred embodiments, the elastic film is formed into a three-dimensional structure using a vacuum or pressure differential process. The carrier material covers a predetermined area of the elastomeric film surface and partially embeds or fuses onto the top surface of the elastomeric film material.

A preferred embodiment of the present invention comprises a film laminate wherein the carrier layer comprises a fibrous material. In certain embodiments, the fibrous material comprises non-woven materials, while in other embodiments the fibrous material can comprise woven or loose fibers. One advantage of the present invention is that a uniform layer of fibrous material can be applied to an elastic film during the film making process. Until the present invention, it has not be possible to supply a layer of fibrous material onto an elastic three-dimensional, apertured film to allow the film laminate being formed to retain its elastomeric characteristics.

In the embodiments where the carrier material comprises a fibrous material, the resulting film has the aesthetic appeal of cloth-like fabrics. Further, the film has the dryness aspects of three-dimensional formed films which is desirable in such end uses as disposable products and wound dressing or bandages.

According to preferred embodiments of the present invention, the thermal energies of both the molten or semi-molten polymeric elastomeric film material and the carrier material are precisely controlled at the point in time when the elastomeric film is subjected to a pressure differential for forming the three-dimensional structure of the film. The thermal energies of the film material and carrier material are controlled such that the heat transfer (which is required to achieve the bond between the elastomeric film material and the carrier material) does not detract from the ability of the elastomeric film material to be further formed into its three-dimensional structure.

In embodiments where the carrier material comprises a fibrous material, portions of the fibrous material become embedded in, or fuse into or onto, the top surface of the film without distortion or loss of the integrity of the fiber. The fibrous material embeds or fuses onto the top surface of the elastomeric film as the three-dimensional structure of the film is being formed such that a fibrous coated three-dimensional apertured elastic film laminate is produced. The resulting film laminate has high stretch or elongation in the cross direction and good breathability characteristics and increased aesthetic value.

In certain embodiments, the relative positions of the film extrusion die and the point of lamination of the film material and carrier material are varied to achieve the bond strengths needed to laminate the carrier material and the elastomeric film material together while maintaining the elastic properties of the film material. The precise location or impingement point at which the carrier material is delivered onto the top surface of the molten or semi-molten elastomeric film material can occur prior to or subsequent to the formation of the three-dimensional structure of the film. In various embodiments, the carrier material is delivered onto the top surface of the molten or semi-molten elastomeric film material at a point in time prior to the three-dimensional structure of the film being formed. In another embodiment, a layer of the carrier material is melt bonded to a top surface of the molten or semi-molten elastic film material at a point in time after the formation of the three-dimensional characteristics of the elastic film.

In a preferred embodiment, the precise location or impingement point of carrier material-to-film material is chosen such that various operating conditions are met. The contact temperature and contact pressure between the carrier material and the elastomeric film material are regulated. The location of the impingement of the carrier material onto the elastomeric film material is regulated such that the carrier material does not touch the molten or semi-molten elastomeric film material prematurely, but only at a desired impingement point.

In a preferred embodiments, the impingement point is located at a predetermined distance from the point at which the pressure differential is supplied to the bottom surface of the elastomeric film material. The carrier material is delivered onto the top of the elastomeric film material without interfering with the formation of the three-dimensional structures being formed in the film material. The pressure differential is regulated such that the three-dimensional structures are apertured such that the elastic film laminate is breathable.

The carrier material supplies additional resistance to the fluid or air displacement across the pressure differential. As the elastomeric film/carrier material laminate passes across the pressure differential, the amount of pressure differential is regulated to compensate for the additional resistance resulting from the presence of the carrier material laminated to the top surface of the elastomeric film material. In a preferred embodiment, the carrier material is supplied onto the elastomeric film material in a manner such that there is minimal, if any, obstruction or resistance to air flow or to the pressure differential being used to form the three-dimensional structures in the film material.

In preferred embodiments, the three-dimensional structures being formed are expanded protuberances or apertures in the elastomeric film. Thereafter, sufficient heat is removed to a point below the temperature of solidification or hardening temperature of the material before the elastomeric film material/carrier material laminate is removed from the pressure differential.

The present invention can be practiced using a batch process using premade rolls of carrier material such as fibrous web materials and/or film-type carrier materials. The present invention can also be practiced using a continuous supply of carrier material such as individual fibers or fibrous webs introduced onto the film material. The present invention can further be practiced using a continuous supply of a film of the carrier material which is co-extruded or introduced onto the elastomeric film material. In certain other embodiments, the carrier material can be supplied onto the elastomeric film material to form a laminate which is apertured in a secondary process.

It is further within the completed scope of the present invention that the elastic film laminate of the present invention can comprise a multilayer structure comprising a first layer of a carrier material, a layer of a elastomeric, three-dimensional film material, and a third layer of a carrier material.

In certain preferred embodiments, the carrier material comprises less than about 40% of the effective thickness of the combined elastomeric film/carrier material laminate. In certain other embodiments, the carrier material can be sufficiently thick to provide an additional function such as cloth-like characteristics and/or absorbent or liquid acquisition and transmission properties to the elastic film laminate. In other embodiments, the carrier material is sufficient thin to mainly provide separation of the stretchy elastomeric film from the processing equipment both during the processing and the end use applications of the film (i.e., when the elastic film laminate is being incorporated into a finished product).

In certain embodiments, the carrier material comprises a film that exhibits low to moderate levels of elasticity such as polyethylene, polypropylene, ethylene vinyl acetate and other such polymeric materials. It is to be understood that the carrier material can include other ingredients such as anti-block and anti-slip ingredients. It is further understood that the carrier material can comprise more than one layer and that the carrier material can be a co-extruded film material. Each layer of the co-extruded carrier material can have different properties which enhance the lamination of the carrier material to the elastomeric film and/or provide other advantages to the laminate film.

In certain embodiments where the carrier material comprises a fibrous material, it is within contemplated scope of the present that the fibrous materials can include polyesters, polyolefins, acrylics, rayons, cottons and other cellulose materials, and blends of the same. The fibrous materials can also include bi-component fibers having an inner core of one material and an outer core of a second material, adhesive fibers, as well as fibrous materials having fibers of different geometries, lengths, diameters and surface finishes. The fibrous material can comprise loose fibers, woven materials and non-woven materials which have different basis weights, fiber compositions, fiber lengths, and which can be made using different processes.

In certain embodiments, the elastomeric film material can comprise a material which is considered highly stretchable and which reverts to its original or nearly original form upon release of any pressure or force applied to the film material. Elastomeric materials which are useful in the present invention include polyolefin type materials such as polyethylene elastomers, and polyurethane films. In preferred embodiments, the preferred elastomeric film material is capable of achieving essentially fully recovery after being stretched at least about 300 to about 400% of its original length. Suitable stretchable elastomeric films comprise natural polymeric materials and synthetic polymeric materials including isoprenes, butadiene-styrene materials and other elastomers. Other suitable elastomers comprise styrene block copolymers such as styrene/isoprene/styrene (SIS), styrene/butadiene/styrene (SBS), or styrene/ethylene-butadiene/styrene (SEBS) block copolymers. Blends of these polymers alone or with other modifying elastic or non-elastomeric materials are also contemplated being useful with the present invention. In certain preferred embodiments, the elastomeric materials can comprise such high performance elastomeric material such as Kraton® elastomeric resins from the Shell Chemical Co., which are elastomeric block copolymers.

DETAILED DESCRIPTION OF THE PRESENT INVENTION

The present invention relates to a three-dimensional, breathable elastic film laminate comprising an elastomeric film and a carrier material adhered thereto. The laminate is particularly useful as a layer in disposable products including absorbent products and wound dressings and the like. However, the present invention is not limited to such applications and the film laminate of the present invention may be use advantageously to produce other products comprising an elastomeric film having desired high stretch characteristics. For ease of illustration, a film laminate comprising a fibrous web carrier material adhered to a three-dimensional elastomeric film is described in detail herein in FIGS. 1 and 2. However, this detailed description will allow those skilled in the art to adapt this invention to produce elastomeric film laminates for other applications.

Figure 1:
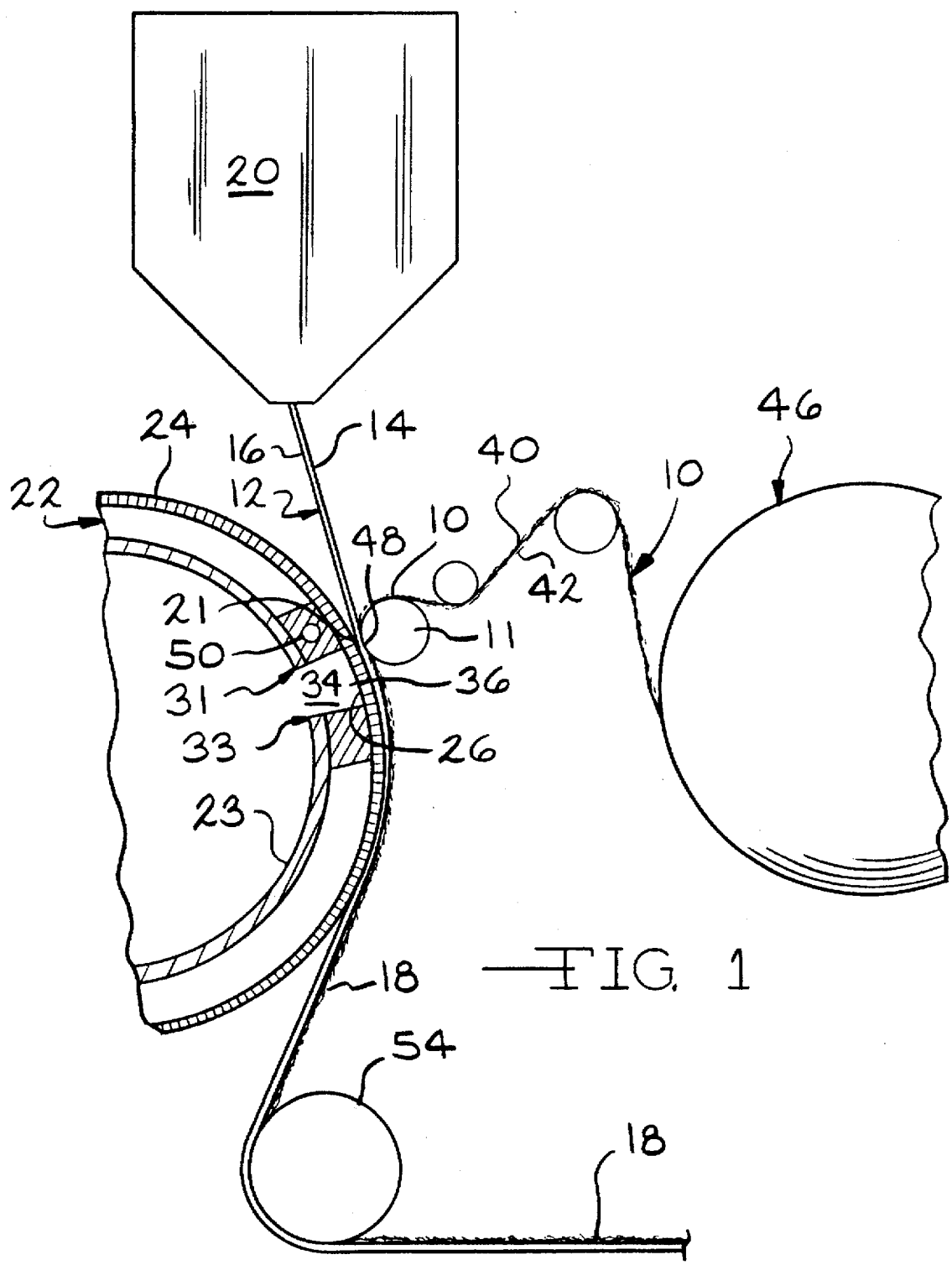
FIG. 1 is a simplified cross-sectional schematic illustration of a process for producing an elastomeric film/carrier material laminate.

FIG. 1 is a simplified schematic illustration showing a process to adhere a predetermined amount of a fibrous carrier material 10 onto a molten or semi-molten elastomeric web or film 12 having a top surface 14 and a bottom surface 16. The fibrous material 10 is applied over a nip roll 11 to the top surface 14 of the film material 12 to form a breathable, elastic three-dimensional formed film/carrier material laminate 18.

In the embodiment shown, the film material 12 is dispensed from a film die 20, preferably at a distance of about 1 to about 10 inches, and most preferably about 2 to about 4 inches, from a point of contact 21 on a screen or film forming means 22. The film material 12 is delivered at an elevated temperature as a molten or semi-molten plastic or polymer resin mass, and in certain embodiments is delivered at a temperature of about 350° to 600° F. (175° C.–315° C.). The film material 12 is formed and perforated by passing a stream of the film material 12 over the film forming means 22 and a pressure differential means 23. It is to be understood that the film forming means 22 can be a conveyor belt type of apparatus (not shown) or other pressure differential means which moves the film material 12. For the ease of illustration, the film forming means 22 is depicted herein as a screen or drum. The film forming means 22 has a rotating surface 24 which is highly perforated with a plurality of apertures 26 extending therethrough. The apertures 26 can be randomly spaced on the surface 24 or can form a predetermined pattern for aesthetic and/or functional requirements. The apertures 26 allow a fluid such as air to pass through the surface 24 of the film forming means 22. The film forming means 22 generally includes a leading edge of a seal 31 and trailing edge of a seal 33 which define a vacuum chamber 34. In certain preferred embodiments, the distance between the seals 31 and 33 ranges from about 0.25 to about 6 inches and in certain embodiments is about 1.5 inches. When the film forming means 22 is a screen, as shown in the figures herein, it is preferred that the perforated surface 24 rotate over the seals 31 and 33. The vacuum chamber 34 is located within the film forming means 22 and is utilized to create a pressure differential between the top surface 14 and the bottom surface 16 of the film material 12.

Figure 2:
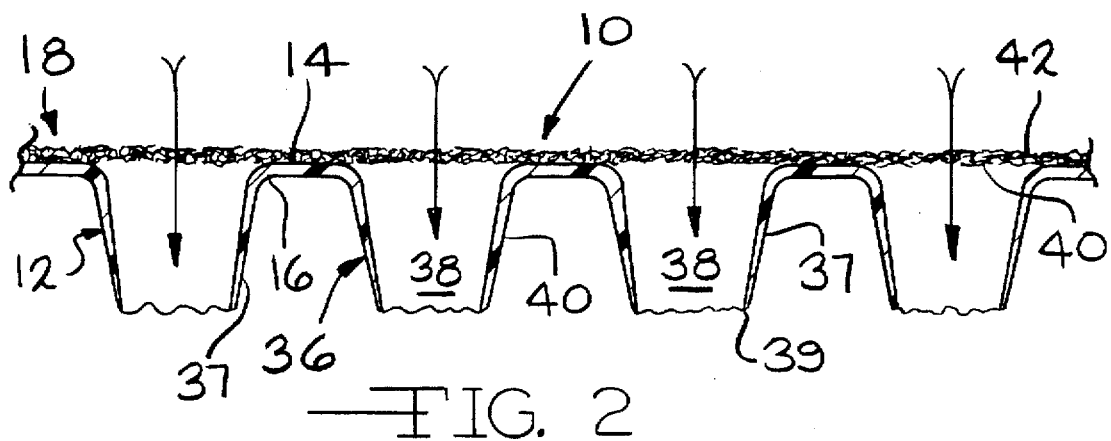
FIG. 2 is a greatly enlarged simplified cross-sectional schematic illustration of a three-dimensional formed elastomeric film having a fibrous material laminated thereto as a carrier material.

As the elastomeric film material 12 is extruded from the die 20, the film material 12 comes into contact with the rotating perforated surface 24 of the film forming means 22. The rotating perforated surface 24 of the film forming means 22 moves continuous portions of the film material 12 across the vacuum chamber 34. The pressure differential caused by the vacuum chamber 34 pulls portions of the film material 12 which are adjacent the apertures 26 in the surface of the screen 24 into the apertures 26 and causes a plurality of three-dimensional structures or protuberances 36 to be formed in the elastomeric film material 12 at the points adjacent the apertures 26 in the screen 24. As seen in FIG. 2, each protuberance or structure 36 has sidewalls 37 and has an aperture 38 at a distal end 39 thereof. The distal end 39 is in a spaced apart relationship to the top surface 14 of the film 12.

Referring again to FIG. 1, the carrier material 10 has a first surface 40, which is brought into contact with the top surface 14 of the film 12, and an opposing, second surface 42. The carrier material 10 has a desired density and layered thickness which is defined by the distance between the first and second surfaces 40 and 42 of the carrier material 10. In certain embodiments, it is advantageous to use a carrier material 10 which comprises a film material which applied to the film material 12 in a continuous process (not shown). In other embodiments, it is advantageous to use fibrous material as the carrier material 10. The carrier material 10 is supplied onto the elastomeric film 12 at a desired tension and rate. In various embodiments, the carrier material 10 is very thin and fragile and is transferred to the elastomeric film 12 under almost no tension to avoid breakage of the carrier material 10. In other various embodiments, the carrier material 10 can have a thicker cross-sectional width or thickness such that the carrier material 10 provides additional desirable characteristics to the laminate 18.

A dispensing means 46 transfers the carrier material 10 to an impingement or lamination point 48 where the carrier material 10 and the elastomeric film 12 contact each other to form the laminate 18.

In the embodiment shown in FIG. 1, the carrier material 10 contacts the elastomeric film 12 at the impingement point 48 prior to the leading edge 31 defining the vacuum chamber 34. In certain embodiments, a temperature control means 50 is positioned inside leading edge seal 31 at a point near where the carrier material 10 contacts the film 12. In the embodiment shown, the temperature control means 50 is shown as a rod heater. The nip or impingement roll 11 can also be temperature controlled to add heat or cooling as desired. However, it is to be understood that other temperature control means, including other heating means or cooling means, can be used to adjust the temperature of the elastomeric film 12 and carrier material 10 at this point. The carrier material 10 embeds partially into and/or melt fuses onto the elastomeric film 12.

The impingement roll 11, in certain embodiments, has a preferred diameter. If the impingement roll 11 has too large a diameter, the impingement roll 11 may either block needed air flow into the vacuum slot 34, or cause the carrier material 10 to touch the molten film material 12 too early, or both. It is desired that the carrier material 10 not be introduced too early onto the molten material 12 such that the carrier material 10 does not melt together or embed too deeply into the film 12. It is also desired that the carrier material 10 not be introduced too late into the melt stream of the film material 12 such that the film 12 cools too early and the carrier material 10 does not sufficiently bond to the film material 12. Further, in certain embodiments, the impingement roll 11 provides sufficient pressure to help embed the first surface 40 of the carrier material 10 at least partially into the top surface 14 of the film 12 at the impingement point 48.

At least one further roller 54 can be provided to aid in removing the successive portions of the elastomeric film/carrier material laminate 18 from the film forming means 22. In certain embodiments, it is contemplated that the roller 54 can be a cooling roller to remove residual latent heat from the laminate 18.

According to embodiment shown in FIG. 1, there is lamination of the carrier material 10 to the material 12 before the film 12 enters the vacuum chamber 34 or is subjected to the pressure differential such that the resulting laminate 18 has both a high elongation and a desirable tensile strength for handleability of the laminate 18.

In certain embodiments, the temperature control means 50 and the impingement roll 11 are adjusted to achieve the proper balance of heat transfer to the elastomeric film 12 and the carrier material 10 in order to counteract any negative heat flux in the film 12 which occurs when the carrier material 10 contacts the elastomeric film 12. The proper balance of heat energies ensures good bonding of the carrier material 10 to the elastomeric film 12. The elastomeric film 12 and the carrier material 10 are then delivered to the vacuum chamber 34 at an optimum temperature to enable a plurality of three-dimensional structures 36 and apertures 38 to be formed in the elastomeric film 12 as portions of the elastomeric film 12 move across the vacuum chamber 34.

The temperature at the lamination point 48 of the carrier material 10 to the elastomeric film 12 is regulated such that the carrier material 10 adheres to the elastomeric film 12 without destroying or damaging the elastic properties of the elastomeric film 12, while still providing the elastomeric film 12 with the desired breathability and handleability properties, such as tensile strength.

According to the present invention, the carrier material 10 adheres to the elastomeric film 12 without the use of adhesives. The molten state of the film 12 is maintained such that the film 12 can be readily formed into a three-dimensional formed film 12. The film material 12 is molten or semi-molten which means that the thermoplastic melt stream of the elastomeric film material is at a temperature above the temperature of melting ($T_m$) of the thermoplastic film material. The temperature of melting of polymers is determined on a Differential Scanning Calorimeter. When the polymer stream is in the molten or semi-molten phase, the polymer is amorphous; that is, molecules comprising the elastomeric polymer are free to move about, particularly when influenced by outside forces such as a pressure differential. Portions of the elastomeric film 12 that form the three-dimensional structures 36 are pulled in the Z direction by the pressure differential force. The portions of the film 12 conform to the shape of the apertures 26 in the surface 24 of the pressure differential means 22. The film 12 is held within the apertures 26 until the elastomeric material at least partially sets or crystallizes. At that time, the film 12 is no longer formable and the film retains its new shape with the three-dimensional structures 36 therein. This phase is known as the temperature of crystallinity (Tc) and is also determined by a Differential Scanning Calorimeter. After the three-dimensional structures 36 and apertures 38 are formed in the film 12, the film 12 releases enough heat energy to move below the temperature of crystallinity, while still being held in its new (three-dimensional) shape by the pressure differential.

The addition (or removal) of heat at the point of impingement (lamination) between the carrier material 10 and the elastomeric film 12 enhances the mechanical bonding and melt fusing by adding a positive (or negative) heat flux to counteract the negative (or positive) heat flux caused by the contact of the elastomeric film with the carrier material. It is also contemplated that heat can be added or removed from the carrier material itself. The amount of heat supplied to or removed from the elastomeric film and the carrier material is dependent upon both the mass of the elastomeric film and the carrier material and the heat retention qualities of the film and the carrier material.

In certain embodiments, when the carrier material 10 comprises a fibrous material, the fibrous carrier material 10 acts as a resistor to air flow through the vacuum chamber 34. More fluid volume (i.e., more air or a greater pressure differential) is drawn across the vacuum chamber 34 of the pressure differential means 22 in order to form and cool the film material 12. The vacuum pressure depends on the thickness of the fibrous carrier material 10 being applied to the top surface 14 of the film 12. In preferred embodiments, between about 10 to about 20% more air is drawn across the vacuum chamber 34 when the fibrous carrier material 10 is applied to the film 12, versus when a film type carrier material is being applied to the film 12. This fluid volume is regulated such that the film 12 is cooled to allow formation of the three-dimensional structures 36 in the film 12 without substantially removing heat from the screen 24. Too much heat removed from the screen 24 will cause the film material 12 on the screen 24 to cool too rapidly, thus preventing good adherence of the carrier material 10 on the top surface 14 of the film 12 and further preventing the three-dimensional structures 36 and apertures 38 from being formed in the film 12.

It is to be understood that various elastomeric polymers have different melt temperatures and that the distance between the die 20 and the impingement point 48 can be varied based on the parameters defined by the use of a particular polymer. Thus, the impingement point of the film will depend on the melting temperature of the specific polymer in use at the time.

In another example, the thermal balance (which is achieved by the heat transfer that occurs) requires a certain amount of time to lapse. Thus, the distance between the leading seal edge 31 and the trailing seal edge 33 defines a predetermined vacuum gap distance. Hence, the time is determined by the speed of rotation of the screen 24 over the vacuum chamber 34 and the distance between the leading edge 31 and trailing edge 33 of the vacuum chamber 34. Therefore, if one wishes the process to go faster, one must increase the distance between the leading edge seal 31 and the trailing edge seal 33 in order to maintain a minimum desired time factor necessary for the proper heat transfer to occur. The parameters defined herein relating to melt temperatures, melt stream length and vacuum slot distance are one set of combinations which can be varied in order to achieve the film of the present invention. However, other parameters relating to impingement point positioning can also be varied, as described herein.

Another parameter is the compression or pressure of the carrier material 10 against the film 12 while the carrier material 10 and film 12 are at the impingement point 48 between the screen 24 and the impingement roll 11. In preferred embodiments, the gap at the impingement point 48 between the impingement roll 11 and the screen 24 is sufficiently wide so that the compressive force initially comprises the weight of the film 12 and, subsequently, the compressive force provided by the air flow through the film 12 as the apertures 38 are formed. The optimum compression is about 5 to about 50% of the ambient loft of the carrier material 10. In certain embodiments, the resiliency of the fibers under compression (i.e., the fact that the fibers tend to straighten back up to their original shape and position they had prior to any compression at the impingement point) will force a portion of their fiber length to embed in the soft molten polymer directly beneath them. Too much compression will force too many fibers to deeply embed or distort and the desired cloth-like characteristics of the end product are lost. In addition, too much compression causes problems such as having the impingement roll 11 bounce, which then causes provide an uneven lamination of the carrier material 10 onto the film material 12. Alternatively, if too little compression is used, there is not enough force to cause sufficient embedding of the carrier materials such that the carrier material is not laminated adequately and will fall or peel off the end product.

In preferred embodiments of the present invention, the impingement roll 11 is spaced at a predetermined distance from the screen 24. A gap generally defines the distance between the roll 11 and the screen 24. The preferred distance of the gap between the roll 11 and screen 24 is determined by the effective thicknesses of elastomeric film 12 and the carrier material 10 being laminated together. It is to be understood, however, that in certain other embodiments, the gap is greater than the effective thickness of the elastomeric film 12 and the carrier material 10. In certain other embodiments, the length of the gap is slightly less than the effective thicknesses of elastomeric film 12 and the carrier material 10. As the elastomeric film 12 and the carrier material 10 pass through the gap, the effective thicknesses of the elastomeric film 12 and the carrier material 10 are reduced somewhat. In certain embodiments, the length of the gap can range from about 50% to about 500% of the effective thicknesses of the film material 12 and the carrier material 10 being laminated together. In certain embodiments, the gap exceeds 100% when the film 12 weight is providing the compressive force (as stated above). In various embodiments, the gap is about 75% to about 95% of the effective thickness of the film material 12 and the carrier material 10. As the carrier material 10 is brought into contact with the top surface 14 of film material 12, significant bonding occurs between elastomeric film material 12 and the carrier material 10.

It should be understood that, in other embodiments, the impingement roll 11 can be adjacent the trailing edge 33 of the vacuum chamber 34 (not shown) or alternatively, the impingement roll 11 can be placed downstream beyond the trailing edge 33 of the vacuum chamber 34 (not shown). The position of the impingement roll 11 is determined, in part, by the temperature of the elastomeric film material 12 and carrier material 10. In addition, the gap can be adjusted to conform to the relative effective thicknesses of the films.

In certain embodiments, the basis weight of a fibrous material preferably ranges from about 5 to about 150 g/m$^2$; in certain embodiments preferably ranges from about 15 to about 35 g/m$^2$. The lower basis weight fibrous material are particularly useful in producing a high quality fibrous texture on the top surface of the film. Further, the fiber diameter of the fibers can be varied. Thicker fibers are less likely to be pulled into the apertures in the film. However, in certain embodiments thicker fibers may form entangled masses of fibers on the top surface of the film. The pressure differential is preferably adjusted when using finer diameter fibers so that a turbulent fibrous stream is not created before the finer diameter fibers contact the top surface of the film. In addition to varying the pressure differential, the distance between the point where the fibrous material is dispensed onto the top surface of the film can be adjusted to control the amount of fibers fusing onto the forming film.

In certain embodiments, webs of fibrous material are made at a point near the film forming process and then directly bonded to the forming film.

It is within the contemplated scope of the present invention that the carrier material can substantially cover the entire surface of the film, or alternatively, the carrier material can be bonded to selective portions of the film. The selective zones or portions of the film can be readily determined by functional patterns required by the end use application. In applications where selective coverage of the carrier material is to be bonded to the film, the carrier material can be slit, unwound and delivered or channeled over the selected portions of the formed film.

The film can be made with different patterns of apertures having different percentages of open areas hole sizes, hole geometries, materials and surface coatings and treatments. It is also contemplated that various blends of resins used to formulate the film can be used to achieve the desired qualities of the end use product.

In the embodiment shown in FIG. 1, the carrier material is generally dispensed from the roll 46. It should be understood, however, that the carrier material 10 can be supplied in other methods, including directly form a film forming process (not shown). The carrier material 10 shown in FIG. 1 is non-woven fibrous material. However, it should be understood that the carrier material can be a flat or a three-dimensional thermoplastic or non-thermoplastic film.

Figure 3:
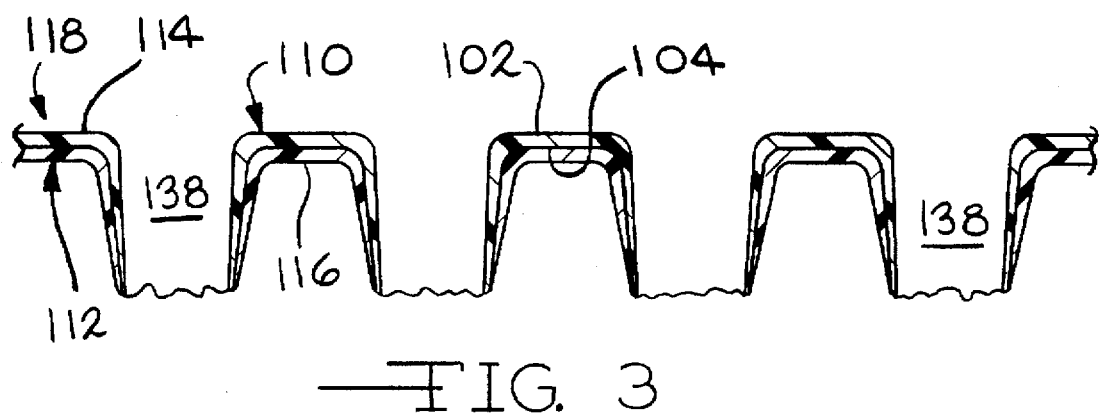
FIG. 3 is a greatly enlarged simplified cross-sectional schematic illustration of a three-dimensional formed elastomeric film having a film material adhered thereto as a carrier material.

Various embodiments of the present invention are shown in FIGS. 2 and 3. It is to be understood, however, that other combinations of laminating an elastomeric film to a carrier material are within the scope of the present invention. In particular, the film material and carrier material can comprise multilayer structures.

FIG. 3 shows a composite laminate material 118 comprising a three-dimensional apertured film 112 having a planar surface 114 and a three-dimensional surface 116. A plurality of three-dimensional structures or protuberances 136 define the bottom surface 116 of the film 112. Each protuberance 136 has side walls 137 and a distal end 139 which defines an aperture 138. A relatively planar or flat carrier material 110 having a upper surface 102 and a lower surface 104 is laminated to the three-dimensional apertured film 112 such that the planar surface 114 of the film 112 and the lower surface 104 of the carrier material 110 are laminated together.

Table 1 provides examples of laminates comprising breathable elastomeric three-dimensional films bonded to non-woven (NW) carrier materials. As can be seen, the tensile strength, the % of elongation, the % stress and porosity of the web show that the web has good converting properties.

The percent of permanent set and the percent of force relaxation at 300% elongation demonstrates the excellent elastic behavior of the laminates of the present invention. In addition, the web porosity data indicate that a wide range of breathability is achievable with the laminates of the present invention.

TABLE I

| Film Blend | Hole Pattern | Film Thickness (micron) | NW Basis Weight & NW Type | Hysteresis 300% Elongation | | TD Force at 100% Elongation (g/cm) | Web Porosity (CFM/sq.ft.) |
|---|---|---|---|---|---|---|---|
| | | | | Tensile Set (%) | Force Relaxation (%) | | |
| A | 8.75 Hex | 51 | 2.27 gsm SBPP | 6 | 21 | | 215 |
| A | 8.75 Hex | 71 | 2.27 gsm SBPP | 5 | 20 | | 240 |
| A | 8.75 Hex | 89 | 2.27 gsm SBPP | 5 | 20 | | 242 |
| A | 8.75 Hex | 71 | 20 gsm SBPP | 5 | 21 | | 215 |
| A | 8.75 Hex | 71 | 25 gsm SBPP | 5 | 20 | | 165 |
| A | 8.75 Hex | 71 | 31 gsm HEC PP | 6 | 19 | | 224 |
| B | 8.75 Hex | 71 | 18 gsm SBPP | 3 | 21 | 418 | 180 |
| B | 20 Square | 51 | 18 gsm SBPP | 2 | 19 | 390 | 65 |
| B | 20 Square | 71 | 18 gsm SBPP | 3 | 18 | 447 | 43 |
| B | 20 Square | 89 | 18 gsm SBPP | 2 | 16 | 524 | 32 |
| B | 22 Hex | 51 | 18 gsm SBPP | 2 | 17 | 366 | 30 |
| B | 22 Hex | 71 | 18 gsm SBPP | 2 | 16 | 498 | 12 |

FIG. 2 is a simplified enlarged cross-sectional illustration of a embodiment of the laminate 18 of the present invention produced according to the method described above. The laminate 18 provides superior elasticity, handleability and breathability properties for an end product. The present invention incorporates the mechanical durability attributes of the carrier material 10 onto the surface of the apertured elastomeric film 12. The laminate 18 comprises the apertured polymeric film 12 and the carrier material 10. The top surface 14 of the film is substantially planar. The plurality of three-dimensional structures or protuberances 36 define the bottom surface 16 of the film 12. The distal end 39 of each protuberance 36 defines the aperture 38. Each aperture 38 is defined by side walls 37. It is noted that the walls 37 taper from the planar top surface 14 toward the aperture 38 itself. The side walls 37 have a progressively thinning cross-section which is due to the stretching or deformation caused by the pressure differential on the film 12 as the film 12 is moved across the vacuum chamber. The first surface 40 of the carrier material 10 is adhered to the top planar surface 14 of the elastomeric film 12. The carrier material 10 fuses and/or mechanically bonds to the film 12.

In the data set forth in Table I above: Blend A comprises about 94% ABA block copolymer elastomer/5% slip & antiblock concentrate/1% white concentrate. Blend B comprises about ABA block copolymer elastomer/23% polyolefin elastomer/5% slip & antiblock concentrate/1% white concentrate.

The non-woven (NW) basis weight and type are designated as follows: "gsm" is grams per square meter, "SBPP" is spun bonded polypropylene, and "HEC PP" is high elongation, carded polypropylene.

Figure 4:
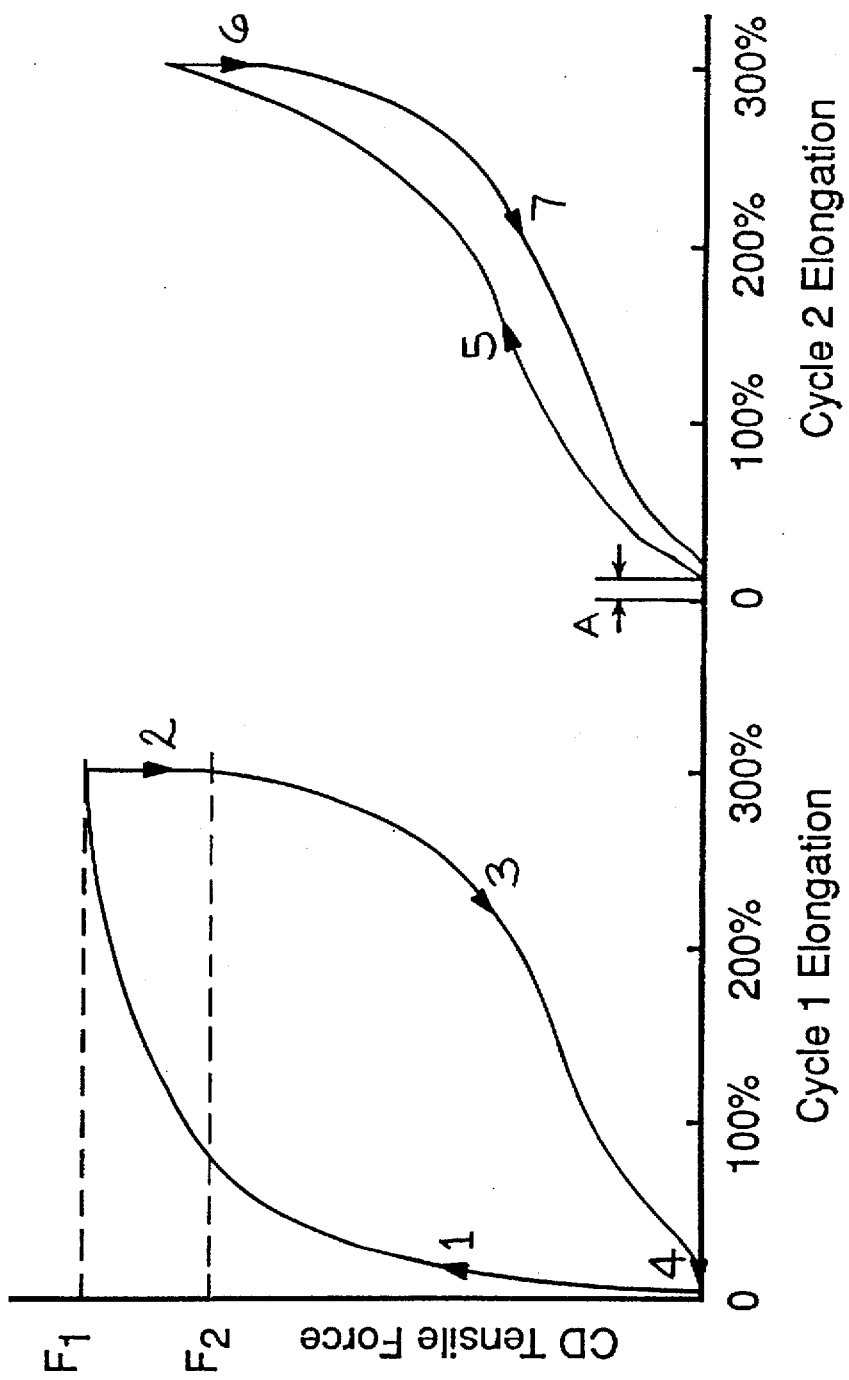
FIG. 4 is a hysteresis diagram showing two cycles of elongation.

Elastic hysteresis is used to quantify elastic performance. The high performance elastic behavior is defined by tensile set less than about 10% and force relaxation less than about 20% after 300 elongation. As shown in FIG. 4, the procedure to measure hysteresis of a sample is as follows:

1) a 1"×3" sample of the film or laminate is placed in the jaws of an Instron.

2) The sample is pulled (1) a first time (cycle 1 elongation) at the rate of 20 inches per minute to the desired elongation (for example, 300%).

3) The force ($F_1$) upon reaching the desired elongation (300%) is noted.

4) The sample is held (2) at the desired elongation (300%) for 30 seconds after which the force ($F_2$) is noted.

5) The instrument is returned (3) to its initial position (zero elongation).

6) The sample is held in a relaxed state for 30 seconds (4).

7) The sample is pulled (5) a second time (cycle 2 elongation) at the rate of 20 inches per minute to the desired elongation (300%). The amount of movement (A) in the Instron jaw before the film exerts any force is noted.

8) The sample is held (6) at the desired elongation for 30 seconds and then relaxed (7).

FIG. 4 is a hysteresis diagram showing two cycles of elongation at 300%. Tensile set is a measure of the permanent deformation of the sample as a result of the initial elongation, hold, and relax cycle. Specifically, tensile set is the ratio of elongation (A) measured in the second cycle divided by the desired elongation (300%). In this example, 8/300=0.0267 or 2.67% set. Force relaxation is defined as the loss in the force as a result of the stretch and hold phases of the first cycle. Mathematically, force relaxation is ($F_1$-$F_2$)/$F_1$ which is typically expressed as a percentage.

The TD Force at 100% Elongation is a measure of the force required to extend the laminate 100% in the transverse (i.e., cross machine) direction. The tensile properties (TD force) were measured using the ASTMD-882 method.

The web porosity data provides a measure of air flow through the laminate. The porosity was measured using the ASTMD-737 method.

While the present invention has been described primarily in the context of a side panel for a disposable absorbent product, it is recognized that the present invention may also be practiced to advantage in many other applications and environments. It will be obvious to those skilled in the art that various changes and modifications can be made without departing from the spirit and scope of the present invention, and it is intended to cover the claims appended hereto. All such modifications are within the scope of this invention.

I claim:

1. A composite material comprising an elastomeric three-dimensional, apertured film having a planar surface and a three-dimensional surface, the three-dimensional surface having a plurality of three-dimensional protuberances wherein each protuberance defines an aperture, and a carrier material bonded to at least the planar surface of the elastomeric film, wherein the film has elastic hysteresis properties such that the film has about 10% or less tensile set and about 21% or less force relaxation after about a 300% elongation.

2. The composite material of claim 1, wherein the carrier material comprises a fibrous material.

3. The composite material of claim 2, wherein the fibrous material comprises a non-woven fabric.

4. The composite material of claim 2, wherein the fibrous material comprises loose fibers.

5. The composite material of claim 2, wherein the fibrous material comprises a woven fabric.

6. The composite material of claim 2, wherein the fibrous material is selected from the group consisting of polyesters, polyolefins, acrylics, rayons, cotton, cellulose materials and blends of the same.

7. The composite material of claim 2, wherein the fibrous material has a basis weight ranging from about 5 to about 150 g/m$^2$.

8. The composite material of claim 7 wherein the basis weight ranges from about 15 to about 35 g/m$^2$.

9. The composite material of claim 1, wherein the carrier comprises at least one layer of a polymeric film including polymeric layers achieved by co-extrusion or extrusion coating.

10. The composite material of claim 1, wherein the elastomeric film is selected from the group consisting of natural polymeric material, synthetic polymeric materials, isoprenes, butadiene-styrene materials, styrene block copolymers, and blends of the same.

11. An absorbent article comprising a topsheet formed of the composite material of claim 1, an absorbent pad and a fluid impervious backsheet.

* * * * *

UNITED STATES PATENT AND TRADEMARK OFFICE
Certificate

Patent No. 5,733,628                                                                                Patented: March 31, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: James E. Pelkie, Terre Haute, IN; John Joseph Curro, Cincinnati, OH; Michele Ann Mansfield, Cincinnati, OH; and George Christopher Dobrin, Mason, OH.

Signed and Sealed this Twenty-first Day of September 2004.

TERREL MORRIS
*Supervisory Patent Examiner*
Art Unit 1771